United States Patent

Toth et al.

[11] 4,201,723
[45] May 6, 1980

[54] DIAMINE-BENZOPHENONES AND A PROCESS FOR THE PREPARATION THEREOF

[75] Inventors: Edit Tóth; József Tőrley; Eva Pálosi; Szaboles Szeberényi; László Szporny; Sandor Görög; Csilla Mészáros, all of Budapest, Hungary

[73] Assignee: Richter Gedeon Vegyeszeti Gyar Rt., Budapest, Hungary

[21] Appl. No.: 808,952

[22] Filed: Jun. 22, 1977

Related U.S. Application Data

[60] Continuation of Ser. No. 658,997, Feb. 18, 1976, abandoned, which is a division of Ser. No. 485,744, Jul. 3, 1974, Pat. No. 3,989,701.

[30] Foreign Application Priority Data

Jul. 26, 1973 [HU] Hungary .................. RI 518

[51] Int. Cl.² ............................................. C07C 97/10
[52] U.S. Cl. .......................... 260/570 AB; 260/404; 260/459 A; 260/561 A; 260/501.18; 260/562 N; 260/567.6 M; 424/316; 424/324; 424/329; 424/33 D
[58] Field of Search ............. 260/570 AB, 501.18

[56] References Cited

U.S. PATENT DOCUMENTS

| | | | |
|---|---|---|---|
| 3,202,665 | 8/1965 | Metlesics et al. | 260/570 X |
| 3,642,897 | 2/1972 | Hardtmann | 260/570 |
| 3,846,477 | 11/1974 | Weldstead et al. | 260/570 X |

Primary Examiner—Robert V. Hines
Attorney, Agent, or Firm—Karl F. Ross

[57] ABSTRACT

New compounds of the formula (I)

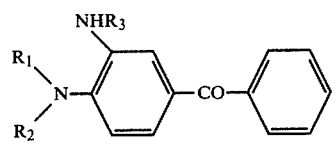

wherein $R_1$ and $R_2$ each is a saturated or unsaturated, straight-chained or branched alkyl group, an aralkyl group, a saturated or unsaturated cycloalkyl group or an aryl group, or $R_1$ and $R_2$ together with the adjacent nitrogen atom forms a substituted or unsubstituted heterocyclic group with or without a further oxygen or nitrogen heteroatom, and $R_3$ is hydrogen or an acyl group derived from a $C_{1-18}$ carboxylic acid. The compounds are prepared by reducing the corresponding nitro compounds of the formula (II)

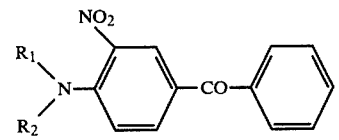

and optionally acylating the obtained product.

The compounds of the formula (I) and their acid addition salts and quaternary ammonium salts are active primarily in the induction of liver microsomal enzymes, but they also possess valuable antipyretic activity and a yohimbine lethality increasing effect characteristic of antidepressants.

8 Claims, No Drawings

DIAMINE-BENZOPHENONES AND A PROCESS FOR THE PREPARATION THEREOF

CROSS REFERENCE TO RELATED APPLICATIONS

This application is a continuation of Ser. No. 658,997 filed Feb. 18, 1976 as a division of Ser. No. 485,744 of July 3, 1974 (now U.S. Pat. No. 3,989,701 (issued Nov. 2, 1976).

This invention relates to new diamino-benzophenones of pharmaceutical activity, to physiologically acceptable acid addition salts and quaternary ammonium salts thereof, and furthermore to a process for the preparation of such compounds.

The compounds according to the invention correspond to the formula (I)

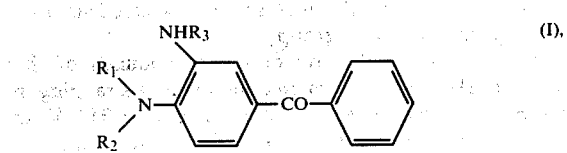

wherein
$R_1$ and $R_2$ each is a saturated or unsaturated, straight-chained or branched alkyl group, an aralkyl group, a saturated or unsaturated cycloalkyl group or an aryl group,
$R_3$ is hydrogen or an acyl group derived from a $C_{1-18}$ carboxylic acid.

$R_1$ and $R_2$ can be saturated or unsaturated, straight-chained or branched $C_{1-18}$ alkyl group, (e.g. an alkyl, alkenyl, alkynyl or alkadienyl group), preferably a $C_{1-10}$ group, such as methyl, ethyl, propyl, allyl, butyl, isobutyl, pentyl, isopentyl, hexyl, 1-octen-7-yl, nonyl or decyl group. The aralkyl group is preferably an aryl-$C_{1-4}$ alkyl, more preferably phenyl-$C_{1-4}$ alkyl, e.g. benzyl, phenethyl, 1-naphthylethyl or 3-phenyl-propyl. The saturated or unsaturated cycloalkyl may be, for example, cycloalkyl, cycloalkenyl, cycloalkynyl or cycloalkadienyl, preferably a $C_{3-8}$ mono carbocycle, such as cyclopropyl, cyclopentyl, cyclohexyl, cyclohexenyl, cycloheptyl etc. The aryl is preferably phenyl or a substituted phenyl of the formula $C_6H_4X$, wherein X is halogen (e.g. fluorine, chlorine, bromine or iodine), alkyl as listed above, e.g. methyl, ethyl, hexyl or decyl, alkoxy, e.g. methoxy, ethoxy, propoxy, butoxy, isobutoxy or decyloxy, or the like.

The compounds of the formula (I) and their salts possess valuable pharmacological properties. According to our experiments these compounds are active primarily in the induction of liver microsomal enzymes, but they also possess valuable antipyretic activity and a yohimbine lethality increasing effect characteristic of antidepressant activity. As reference substances, phenobarbital, phenacetine and imipramine [5-(3-dimethylamino-propyl-10,11-dihydro-5H-dibenz(b,f)azepin] were used in the experiments.

The pharmacological tests were carried out as follows:

To investigate the enzyme inductive effect, Wistar female rats, each weighing 40 to 50 g. were treated with pure solvent, or with a dosage of 60 mg./kg. of phenobarbital or the compound to be tested, respectively. 24 hours after this treatment 40 mg./kg. of hexobarbital were administered intravenously into the animals. The decrease of the elimination period and the liver enzyme induction was expressed as the shortening of duration of sleeping. The results of these tests are given in Table 1.

To test the antipyretic effect, a 15% yeast suspension was administered to male rats each weighing 180±10 g. No food was given to the animals, they could consume, however, arbitrary amount of water. 16 hours after the administration of yeast the rectal temperature of the animals was taken, and the animals were treated with pyragro in an intravenous dosage of 50 M bact./animal. The compound to be tested was administered orally into the animals, thereafter the change in rectal temperature both for the treated and the control animals was recorded for 5 hours, using an "Elab" type electrothermometer. Phenacetine, used as reference substance, and the compounds of the invention were administered in dosages of 40 mg./kg. body weight. The results of this test are listed in Table 2.

To investigate the yohimbine-potentiating effect, CFLP male mice each weighing 20 to 25 g. were treated orally with the compounds according to the invention, and 1 hour after this treatment yohimbine was injected subcutaneously into the animals in a dosage of 20 mg./kg. 24 hours after the introduction of yohimbine the perished animals were counted, and the yohimbine potentiating effect ($ED_{50}$) of the compounds was calculated from these data by probit analysis. As reference substance, imipramine was used. The results of this test are given in Table 3.

In Tables 1 to 3 the following abbreviations are used:
$C_3$ = 3-amino-4-(N-methyl-piperazino)-benzophenone
$C_6$ = 3-amino-4-(N-ethyl-N-phenylamino)-benzophenone
$C_7$ = 3-amino-4-(N,N-diisobutylamino)-benzophenone
$C_8$ = 3-amino-4-morpholino-benzophenone
$C_{11}$ = 3-propionylamino-4-morpholino-benzophenone HCl
$C_{12}$ = 3-palmitoylamino-4-morpholino-benzophenone
p.o. = per os
S.E. = standard error Table 1

| | Inductive effect | |
|---|---|---|
| Compound | Dosage mg./kg. p.o. | Average duration of sleeping ± S.E., minutes |
| Control | — | 27.4 ± 3.02 |
| Phenobarbital | 60 | 5.4 ± 1.63 |
| $C_6$ | 60 | 11.5 ± 2.71 |
| $C_7$ | 60 | 10.0 ± 1.92 |
| $C_{11}$ | 60 | 9.0 ± 1.30 |
| $C_{12}$ | 60 | 10.4 ± 1.02 |

Table 2

| | Antipyretic activity | |
|---|---|---|
| Compound | Dosage mg./kg. | Decrease of temperature °C. |
| Phenacetine | 40 | −1.0 |
| $C_8$ | 40 | −1.0 |

Table 3

| Potentiation of yohimbine lethality | |
|---|---|
| Compound | $ED_{50}$ mg./kg. p.o. |
| Imipramine | 9.0 |

Table 3-continued

| Potentiation of yohimbine lethality | |
|---|---|
| Compound | $ED_{50}$ mg./kg. p.o. |
| $C_3$ | 30.0 |

Inductive effect: $LD_{50}$ mg./kg. p.o.: phenobarbital: 240.0; $C_6$: above 400; $C_7$: above 600; $C_{11}$: above 450; $C_{12}$: above 500.
Antipyretic activity: $LD_{50}$ mg./kg. p.o.: phenacetine: 2045; $C_8$: above 3000.
Potentiation of yohimbine lethality: $LD_{50}$ mg./kg. p.o.: imipramine: 666; $C_3$: above 3000.

As is apparent from the above data, the compounds tested possess valuable activities in three fields, namely as microsomal enzyme inducers, antipyretics and antidepressants. The activities of these compounds are marked and extremely selective.

Thus, for example, compound $C_{11}$ has an enzyme-inducing effect, the same in strength as for phenobarbital, but has no effect on the central nervous system, hence it can be used more advantageously than phenobarbital.

Compound $C_8$ is similar in antipyretic activity to phenacetine, but the former has no harmful effects on the kidneys.

Although compound $C_3$ is inferior in antidepressant activity to imipramine, it can be used to advantage in the therapy, since, unlike imipramine, in the active dosage it causes no ataxis or reflex retardation. ($ED_{50, rota-rod}$: imipramine: 28.0 mg./kg., $C_3$: 160 mg./kg.)

Besides their pharmacological value, the new compounds of the invention can also be used as intermediates in the syntheses of pharmacologically active substances.

The compounds of the formula (I), wherein $R_1$, $R_2$ and $R_3$ each have the same meanings as defined above, can be prepared according to the invention by reducing a compound of the formula (II)

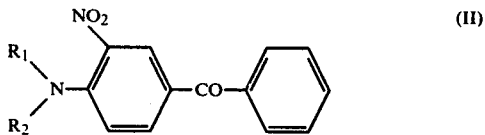

wherein $R_1$ and $R_2$ are as defined above, and, if desired, acylating the obtained substance with a $C_{1-18}$ carboxylic acid or a reactive derivative thereof. If desired, the thus-obtained free bases are converted into their acid addition salts or quaternary ammonium salts, or the free bases are liberated from the compounds obtained in the form of their acid addition salts.

As described above, the compounds of the formula (I) are prepared by the selective reduction of the compounds of the formula (II) into the corresponding 3-amino-derivatives, and, if desired, by the acylation of the 3-amino group. In this selective reduction only the nitro group in position 3 is converted into an amino group, with the other parts of the molecule remaining unchanged. The reduction can be carried out by various methods, one of them being the hydrogenation of the compounds of the formula (II) with a calculated amount of hydrogen in the presence of a catalyst promoting the reduction of the nitro group. As the catalyst, e.g. Raney-nickel, platinum or palladium can be used; these latter substances are applied in supported or unsupported form, deposited for instance on activated carbon, an alkaline earth metal carbonate or sulphate, etc.

The reaction is carried out preferably in the presence of an organic solvent, such as benzene, ethanol, tetrahydrofuran or ethyl acetate. The temperature of the reaction is preferably 20° to 50° C.

The reduction can be carried out under atmospheric or higher pressure; the pressure applied is preferably lower than 5 at.

When the reaction has been terminated, the catalyst is removed by filtration, and the product is isolated from the filtrate.

The selective reduction can also be carried out by means of a hydrogen donor substance, such as cyclohexene. According to this method a compound of the formula (II) is dissolved in cyclohexene or in a mixture of cyclohexene and another solvent, such as tetrahydrofuran, and the reaction mixture is refluxed in the presence of a metal catalyst such as Raney nickel or metallic palladium. During this reaction cyclohexene is converted into benzene through the formation of 1,3-cyclohexadiene, and the nitro group is reduced simultaneously into an amino group.

The selective reduction of the compounds of the formula (II) can also be carried out by metals ranging in normal electrode potential from −2.04 to +0.05 V, in the presence of an organic or mineral acid, such as hydrochloric acid or glacial acetic acid, or in some instances in the presence of a base, such as sodium hydroxide.

According to a further method of the invention nascent hydrogen liberated from an alkali metal borohydride, such as sodium borohydride is used for the reduction instead of molecular hydrogen. This reaction is conducted optionally in the presence of a catalyst. According to this reduction method first a platinum, palladium or rhodium salt is reacted with sodium borohydride in the presence of a carbon support in ethanol medium. This process yields a very active catalyst. Then hydrochloric acid and the ethanol solution of the compound of the formula (II) is added to the thus-obtained mixture, and finally the ethanol solution of the stoichiometric amount of sodium borohydride is added dropwise. By the nascent hydrogen liberated from sodium borohydride when contacted with hydrochloric acid, the nitro compound is reduced in some minutes.

The acid amides can be prepared by reacting the compounds containing a primary amino group with a $C_{1-18}$ carboxylic acid or a reactive derivative thereof, preferably an acid halide or anhydride. The acylation can be carried out in an inert organic solvent, such as acetone or dioxane, at a temperature ranging from −10° C. to the boiling point of the solvent, preferably at 20° to 50° C. Inorganic bases or tertiary organic bases can be used to bind the acid liberated in the reaction, the acid binding agent may be, however, the starting benzophenone derivative itself as it contains primary and tertiary amino groups. This reaction leads directly to the salt of a benzophenone of the formula (I), with an acyl group as substituent $R_3$.

The free bases of the formula (I) can be converted into their acid addition salts by reacting them with organic or mineral acids, e.g. hydrochloric acid, hydrobromic acid, sulphuric acid, phosphoric acid, lactic acid, citric acid, tartaric acid, maleic acid or fumaric acid. The free bases can also be converted into the corresponding quaternary ammonium compounds formed with saturated or unsaturated lower alkyl halides, alkyl sulphates, or benzyl halides.

The bases can be liberated from the acid addition salts and quaternary ammonium compounds according to known procedures. The thus-obtained free bases can be, in turn, converted into other acid addition salts or quaternary ammonium derivatives.

The compounds of the formula (II), used as starting substances, can be prepared e.g. by reacting a 3-nitro-4-halo-benzophenone with a secondary amine of the formula (III)

$$R_1-NH-R_2 \qquad (III)$$

wherein $R_1$ and $R_2$ each have the same meanings as defined above.

The compounds according to the invention can be administered to the patients in pharmaceutically active but non-toxic dosages. The actual amount of the active agent to be administered depends on the pharmaceutical effect to be attained, moreover on the method of treatment, as well as on the general condition and sensitivity of the patient to be treated.

The effective dosage can be administered either in subdivided form several times a day, or in time release form.

The pharmacologically active compounds of the invention can be used in the therapy in the form of pharmaceutical compositions. Such compositions suitable for enteral, parenteral or topical administration may contain the new compounds according to the invention in admixture with solid or liquid, organic or inorganic, pharmaceutically acceptable carriers which do not react with the active agents. These carriers include e.g. water, alcohols, gelatine, propylene glycol, vegetable oils, cholesterol, starch, lactose, talc, gum, magnesium stearate, etc. If desired, the pharmaceutical products can be sterilized.

The pharmaceutical compositions may contain auxiliary agents, such as preserving, stabilizing, wetting or emulsifying agents, solubilizing substances, salts or buffers to modify the osmotic pressure, etc. These compositions may contain the compounds of the formula (I) in combination with other therapeutically active agents.

The pharmaceutical compositions are prepared by methods well known in the art. Thus, for example, the injectable compositions are prepared by dissolving an acid addition salt or quaternary ammonium salt of the active agent in pyrogen-free physiological saline solution or in bidistilled water, optionally sterilizing the solution, and filling into ampoules under sterile conditions.

The invention is elucidated in detail by the following non-limiting Examples.

EXAMPLE 1

3-Amino-4-(N,N-diisobutylamino)-benzophenone 10.63 g. of 3-nitro-4-(N,N-diisobutylamino)-benzophenone are dissolved in 106 ml. of ethyl acetate, the solution is poured into a hydrogenating apparatus, and 5,3 g. of Raney-nickel are added. The reaction mixture is hydrogenated at room temperature and atmospheric pressure until the uptake of the calculated amount of hydrogen (this requires generally about 1.5 hours). Thereafter the catalyst is removed by filtration and the clear solution is evaporated to dryness under reduced pressure. The obtained 9.4 g. of solid are recrystallized from isopropanol, to yield pure 3-amino-4-(N,N-diisobutylamino)-benzophenone; m.p.: 59°–60° C.

Analysis for $C_{21}H_{28}N_2O$: Calculated: C, 77.73%; H, 8.70%; N, 8.63%. Found: C, 77.68%; H, 8.55%; N, 8.70%.

I.R. spectrum: characteristic bands appear at 705, 725, 795, 855, 1650, 2820, 2880, 2940, 2960, 3380, and 3480 cm$^{-1}$ U.V. spectrum: $\lambda_{max}.^{EtOH}$ 251, 314, 368 nm.

EXAMPLE 2

3-Amino-4-(N,N-di-n-amylamino)-benzophenone 5.72 g. of 3-nitro-4-(N,N-di-n-amylamino)-benzophenone are reduced as described in Example 1 to yield 5.1 g. of 3-amino-4-(N,N-di-n-amylamino)-benzophenone in the form of a viscous, oily product.

Analysis for $C_{23}H_{32}N_2O$: Calculated: C, 78.36%; H, 9.15%; N, 7.95%. Found: C, 78.41%; H, 9.25%; N, 7.78%.

I.R. spectrum: characteristic bands appear at 715, 730, 795, 855, 1655, 2820, 2860, 2940, 2960, 3360, and 3450 cm$^{-1}$.

U.V. spectrum: $\lambda_{max}.^{EtOH}$ 223, 251, 314, 366 nm.

EXAMPLE 3

3-Amino-4-(N-ethyl-N-cyclohexylamino)-benzophenone 7.1 g. of 3-nitro-4-(N-ethyl-N-cyclohexylamino)-benzophenone are dissolved in a 1:1 mixture of benzene and ethyl acetate, and 0.7 g. of palladiumized carbon are added to the mixture. The mixture is hydrogenated at room temperature and 3 atm. hydrogen pressure until the uptake of the calculated amount of hydrogen (this requires about one hour). Thereafter the catalyst is removed by filtration, and the filtrate is evaporated to dryness under reduced pressure. 6.35 g. of crude product are obtained. After recrystallization from isopropanol, 5.8 g. of pure 3-amino-4-(N-ethyl-N-cyclohexylamino)-benzophenone, melting at 106.5°–107.5° C. are obtained.

Analysis for $C_{21}H_{26}N_2O$: Calculated: C, 78.22%; H, 8.13%; N, 8.69%. Found: C, 78.31%; H, 8.13%; N, 8.62%.

I.R. spectrum: characteristic bands appear at 710, 730, 880, 1645, 2860, 2940, 3370, and 3460 cm$^{-1}$.

U.V. spectrum: $\lambda_{max}.^{EtOH}$ 224, 252, 326, 367 nm.

This compound can also be prepared according to the method described in Example 1.

EXAMPLE 4

3-Amino-4-(N-methyl-N-octylamino)-benzophenone 7.36 g. of 3-nitro-4-(N-methyl-N-octylamino)-benzophenone are reduced as described in Example 1 to yield 6.1 g. of 3-amino-4-(N-methyl-N-octylamino)-benzophenone.

Analysis for $C_{22}H_{30}N_2O$: Calculated: C, 78.06%; H, 8.93%; N, 8.28%. Found: C, 78.00%; H, 8.77%; N, 8.13%.

I.R. spectrum: characteristic bands appear at 700, 720, 800, 880, 1650, 2805, 2860, 2940, 2960, 3360, and 3440 cm$^{-1}$.

U.V. spectrum: $\lambda_{max}.^{EtOH}$ 222, 252, 310, 365 nm.

EXAMPLE 5

3-Amino-4-(N-ethyl-N-phenylamino)-benzophenone 10.39 g. of 3-nitro-4-(N-ethyl-N-phenylamino)-benzophenone are reduced as described in Examples 1 or 2, and the obtained 9.4 g. of crude product are recrystallized from isopropanol. 8.5 g. of 3-amino-4-(N-ethyl-N-phenylamino)-benzophenone are obtained; m.p.: 82°–82.5° C.

Analysis for: $C_{21}H_{20}N_2O$: Calculated: C, 79.71%; H, 6.37%; N, 8.85%. Found: C, 79.88%; H, 6.40%; N, 8.93%.

I.R. spectrum: characteristic bands appear at 695, 735, 740, 750, 795, 850, 1650, 2880, 2940, 2980, 3390, and 3500 cm$^{-1}$.

U.V. spectrum: $\lambda_{max.}^{EtOH}$ 252, 374, 310 nm.

EXAMPLE 6

3-Amino-4-(N-methyl-N-benzylamino)-benzophenone 15.6 g. of 3-nitro-4-(N-methyl-N-benzylamino)-benzophenone are reduced as described in Examples 1 or 2, and the obtained crude solid is recrystallized from methanol. 12.1 g. of 3-amino-4-(N-methyl-N-benzylamino)-benzophenone are obtained, m.p.: 93°–94° C.

Analysis for: $C_{21}H_{20}N_2O$: Calculated: C, 79.71%; H, 6.38%; N, 8.85%. Found: C, 79.58%; H, 6.51%; N, 8.72%.

I.R. spectrum characteristic bands appear at 700, 705, 730, 735, 795, 850, 1645, 2800, 2840, 2860, 2960, 3360, and 3940 cm$^{-1}$.

U.V. spectrum: $\lambda_{max.}^{EtOH}$ 214, 252, 306, 364 nm.

What we claim is:

1. A compound of the formula

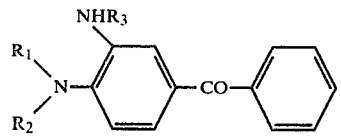

wherein
$R_1$ and $R_2$ each is a $C_1$ to $C_{18}$ saturated or unsaturated, straight-chain or branched alkyl group, an aralkyl group with $C_1$–$C_4$ alkyl, a saturated or unsaturated $C_3$–$C_8$ cycloalkyl group or an aryl group, and
$R_3$ is hydrogen, or a pharmaceutically effective salt thereof.

2. The compound defined in claim 1, selected from the group which consists of
 3-Amino-4-(N,N-diisobutylamino)-benzophenone;
 3-Amino-4-(N,N-di-n-amylamino)-benzophenone;
 3-Amino-4-(N-ethyl-N-cyclohexylamino)-benzophenone;
 3-Amino-4-(N-methyl-N-octylamino)-benzophenone;
 3-Amino-4-(N-ethyl-N-phenylamino)-benzophenone; and
 3-Amino-4-(N-methyl-N-benzylamino)-benzophenone.

3. The compound defined in claim 1 which consists of 3-Amino-4-(N,N-diisobutylamino)-benzophenone.

4. The compound defined in claim 1 which consists of 3-Amino-4-(N,N-di-n-amylamino)-benzophenone.

5. The compound defined in claim 1 which consists of 3-Amino-4-(N-ethyl-N-cyclohexylamino)-benzophenone.

6. The compound defined in claim 1 which consists of 3-Amino-4-(N-methyl-N-octylamino)-benzophenone.

7. The compound defined in claim 1 which consists of 3-Amino-4-(N-methyl-N-benzylamino)-benzophenone.

8. The compound defined in claim 1 which is 3-amino-4-(N-ethyl-N-phenylamino)-benzophenone.